Jan. 12, 1971 P. L. SCOTT Plant Pat. 3,017

FELICIA PLANT

Filed Sept. 11, 1968

INVENTOR.
PAUL L. SCOTT
BY Agnew & Moe
ATTORNEYS.

United States Patent Office

Plant Pat. 3,017
Patented Jan. 12, 1971

3,017
FELICIA PLANT

Paul L. Scott, Duarte, Calif., assignor to Burkard Nurseries, Inc., Pasadena, Calif., a corporation of California Filed Sept. 11, 1968, Ser. No. 759,253
Int. Cl. A01h *5/00*
U.S. Cl. Plt.—68 1 Claim

ABSTRACT OF THE DISCLOSURE

A *Felicia amelloides* characterized by its more compact shape and that the flower heads remain open at night.

This invention relates to a new variety of plant Felicia, which plant has the botanical name *Felicia amelloides*, and is from the Compositae family and Asterae tribe. The plant ordinarily grows to a height of about .3 meter and a spread of about .46 meter or more in a mound or cushion shape.

The present new or improved variety of Felicia is characterized (a) in that the flower heads remain open at night, (b) by its compact shape, and (c) by other characteristics as hereinafter are set forth in the detailed description of the new variety.

The new variety of Felicia plant according to the present invention was developed in Duarte, Calif., and is a third generation from a seed of a "Santa Anita" Felicia from the Los Angeles County Arboretum in Acadia, Calif., cross-pollenized with pollen from the same plant. The "Santa Anita" Felicia is a tetraploid, a sprawling plant with narrow light blue petals, originally from South Africa.

The accompanying drawings show a typical specimen of the plant according to this invention and are depicted in color as nearly true as it is reasonably possible to make the same in a color photograph of this character, in which.

Figure 1:
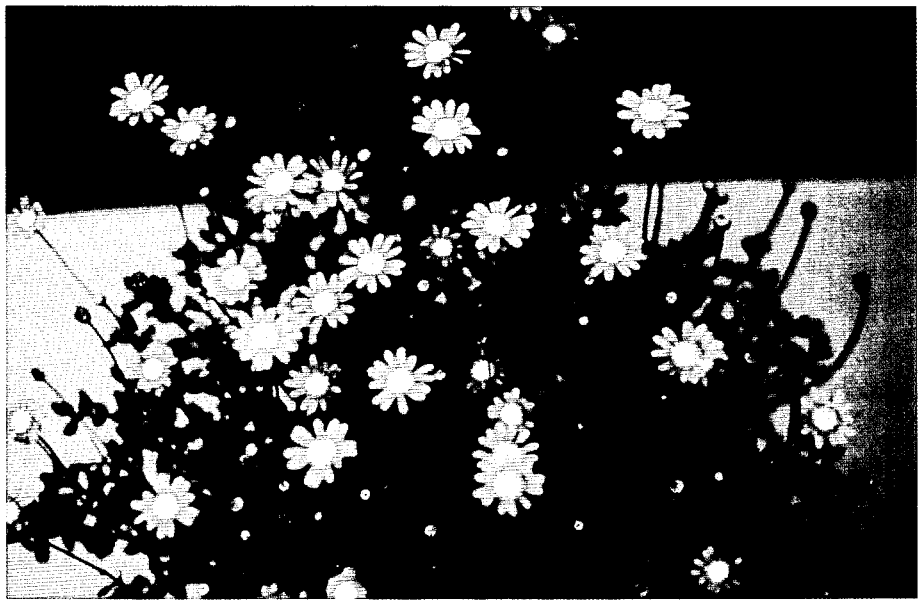
FIG. 1 is a side view of the plant in bloom.
Figure 2:
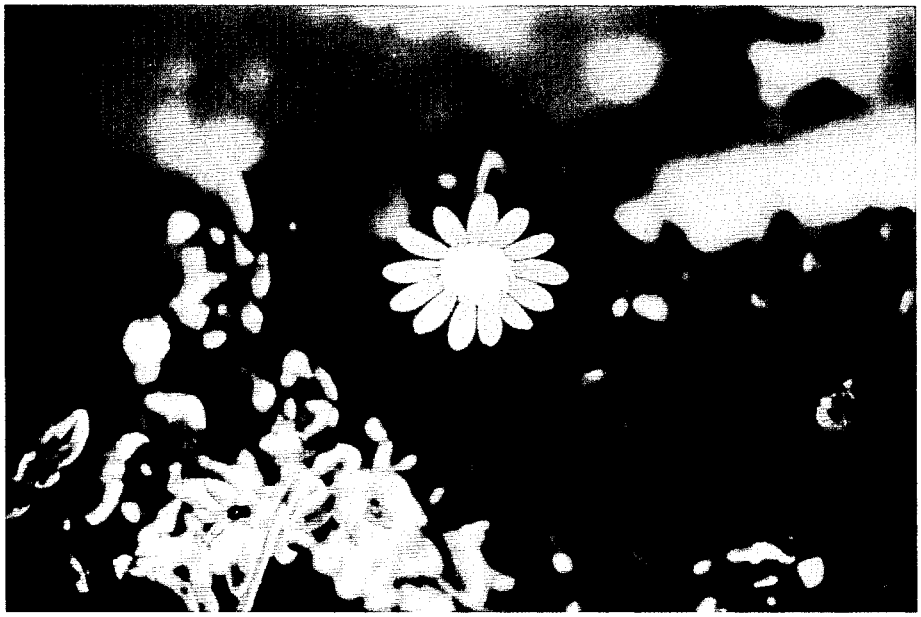
FIG. 2 is a closeup view of a head of flowers.

Each head of flowers of the new variety of plant comprises a plurality of ray flowers disposed somewhat irregularly around a plurality of disc flowers. The ray flowers are each about 1.0 cm. to 1.2 cm. in length and about 5 mm. in width and have an elongate-elliptical shape. About thirteen ray flowers are disposed on each flower head, although that number may vary from head to head. The ray flowers are a substantially uniform violet-blue color, 96A on the Royal Horticultural Society color fans (RHS), when they bloom, fading to about 94B to 96B RHS in about two to three days. The disc flowers each have a width of about 12 mm. and are yellow in color, 13B RHS. The flower color is dependent upon nutrition and temperature range, and poor nutrition or increased temperature will make the flower petals fade sooner. The ray flowers have a matte finish, and the flower head has no fragrance. Each flower head lasts approximately two to three days cut, and three to four days on the plant.

The involucre comprises a single row of bracts, each having a diameter of about 8.0 to 8.5 mm. and a height of about 9 mm.; the body of the bracts are yellow-green (143A RHS) having edges slightly lighter (144A RHS). The capitula are solitary and have a width of about 3.0 to 3.3 cm.

The plant blooms continuously from about late winter to fall in a temperature range of about 45° F. to 85° F. Above 85° F. the plant tends to grow dormant; the plant freezes at about 28° F. The ray flowers stand straight in late bud stage and then lie back during bloom.

The disc flowers produce a golden-yellow pollen on a large number of minute anther stamens on short filament stamens. The ray flowers produce biparted neutral grey or off-white stigmas on small styles which are barely visible. The seeds produced are flat and elliptic, often with a longitudinal ridge on one or both sides. The attachment end of the seed is obtuse and the outer end acute. The seeds are about 2.5 to 3.0 mm. long and about 1.5 to 2.0 mm. wide. The seeds are black (202A RHS).

The stem of the plant is yellow-green (144C RHS) and has a length of about 80 mm. to 3.5 cm. and a width of about 2 to 6 mm. The texture of the stem is puberulent. The peduncles are yellow-green, 144C RHS, and have a length varying between about 12 to 16 cm.

The leaves are arranged on the base alternately and are expetiolate. The leaves are about 2.4 cm. in length, about 1.4 cm. in width, and have a thickness of about 0.5 mm. The upper surfaces of the leaves are green, 137B RHS, and the lower surfaces are green, 138B RHS. The texture of the upper surface of the leaves is slightly scabrous, remotely pubescent, and the upper surface has a depressed midvein, with the other veins slightly depressed. The texture of the leaf surface is slightly punctate, and the lower surface has a raised midvein having a tomentose texture with the other veins slightly tomentose. The edges of the leaves are entire to remotely denticulate, are ciliate and recurved. The shape of the leaves is elliptic-acute having a blunt point, and slightly clasping. The foliage is in abundance.

The new and distinct plant variety has been asexually reproduced in Duarte, Calif., from cuttings of the plant.

The new variety of Felicia plant is vigorous in growth and a profilic producer of blossoms. The plant is a more compact shaped plant than other varieties of Felicia and the flower heads of this new variety remain open at night.

What is claimed is:

1. A new and distinct variety of Felicia plant substantially as herein described and illustrated, characterized as to novelty in that the flower heads remain open at night, and the compact shape of the plant as compared to other varieties of Felicia.

No references cited.

ROBERT E. BAGWILL, Primary Examiner